US00PP35911P2

(12) United States Plant Patent
Clarkson

(10) Patent No.: US PP35,911 P2
(45) Date of Patent: Jul. 2, 2024

(54) ***FRAGARIA* PLANT NAMED 'Eves Joy'**

(50) Latin Name: ***Fragaria* x *ananassa***
Varietal Denomination: Eves Joy

(71) Applicant: Graham Clarkson, Faversham (GB)

(72) Inventor: Graham Clarkson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 18/509,293

(22) Filed: Nov. 14, 2023

(30) Foreign Application Priority Data

Dec. 15, 2022 (QZ) ..... PBR 2022/2995

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/08
See application file for complete search history.

*Primary Examiner* — Keith O. Robinson
(74) *Attorney, Agent, or Firm* — Penny J Aguirre

(57) ABSTRACT

A new and distinct everbearing *Fragaria* plant named 'Eves Joy' that is characterized by its marketable fruit yields early in the season, its fruit with skin that is highly glossy and moderately red in color with firm skin and flesh, its semi-upright growth habit with a moderate to sparse canopy and little to no blistering on its leaves, and its fruit that are sweet and exceptionally juicy and consistently large in size.

3 Drawing Sheets

Botanical classification: *Fragaria* x *ananassa*.
Variety denomination: 'Eves Joy'.

CROSS REFERENCE TO A RELATED APPLICATIONS

This application claims priority to European Community Plant Variety Office (C.P.V.O.) Plant Breeder's Rights Application No. 2022/2995 filed on Dec. 15, 2022, under 35 U.S.C. 119(f), the entire contents of which is incorporated by reference herein. This Application is also related to a Plant Breeder's Rights Application in The United Kingdom, Application No. 10/190 filed on Jan. 2, 2023.

BACKGROUND OF THE INVENTION

The present invention relates to a new and distinct cultivar of *Fragaria*, botanically known as *Fragaria* x *ananassa* 'Eves Joy' and will be referred to hereafter by its cultivar name, 'Eves Joy'. 'Eves Joy' is an everbearing strawberry grown for fruit production.

The new cultivar was derived from an ongoing breeding program conducted by the Inventor at a farm in Faversham, Kent, The United Kingdom. The goal of the breeding program is to develop new cultivars of Strawberry plants with high fruit yields, fruit that has firm skin with good eating quality and low acidity. 'Eves Joy' arose from a controlled cross made by the Inventor in 2015 between an unpatented selection from the Inventor's breeding program, designated as accession number "EQ27" as the female parent and an unpatented selection from the Inventor's breeding program, designated as accession number "JEW35" as the male parent. 'Eves Joy' was selected as a single unique plant in 2016 from amongst the seedlings that resulted from the above cross.

Asexual propagation of the new cultivar was first accomplished by rooting of stolons by the Inventor in Faversham, Kent, United Kingdom in 2016. Asexual propagation by rooting of stolons and tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'Eves Joy' as a new and unique cultivar of *Fragaria*.

1. 'Eves Joy' exhibits high marketable fruit yields early in the season.
2. 'Eves Joy' exhibits fruit with skin that is highly glossy and moderately red in color with firm skin and flesh.
3. 'Eves Joy' exhibits a semi-upright growth habit with a moderate to sparse canopy and little to no blistering on its leaves.
4. 'Eves Joy' exhibits fruit that are sweet and exceptionally juicy.
5. 'Eves Joy' produces fruit that are consistently large in size.

The female parent of 'Eves Joy' differs from 'Eves Joy' in having a denser plant canopy, fruit that is typically smaller in size and less juicy. The male parent of 'Eves Joy' differs from 'Eves Joy' in producing a lower average yield in grams per plant and fruit that is more acidic in taste and has a distinct band around its shoulders that is without achenes.

'Eves Joy' can be most closely compared to the cultivar 'Eves Delight 2' (U.S. Plant Pat. No. 32,418). 'Eves Joy' produces, on average, a greater total and percentage of class 1 fruit per plant than 'Eves Delight 2' and is larger in size with a higher weight per berry. Both have a firm skin and therefore good storage life; however, 'Eves Joy' produces softer and glossier fruit with a higher level of juiciness. The coloring of fruit produced by 'Eves Joy' is a moderate red, making it brighter in colour than 'Eves Delight 2', the fruit of which is a much paler red. The Brix reading is high in the two varieties; however, 'Eves Joy' is usually slightly lower in Brix than 'Eves Delight 2'. Both varieties produce fruit which is absent or near to absent of a band without achenes.

'Eves Joy' has a semi-upright habit and a medium to sparse density of canopy, which results in a moderately sparser appearance than 'Eve's Delight 2'. The leaf color of 'Eves Joy' is also a noticeably a darker shade of green than 'Eves Delight 2', making this a clear distinguishing characteristic between the two varieties. Like 'Eves Delight 2', the leaves of 'Eves Joy' are rounded in shape with an acute base and round apex and a similar level of serration of the leaf margins. The leaves of 'Eves Joy' shows a smaller length to width ratio than 'Eves Delight 2' and on average a lower level of blistering.

The peduncles produced by 'Eves Joy' show a much stronger pubescence than 'Eves Delight 2', while its pedicels possess a weaker coverage of pubescence and are typically shorter in length. In both varieties, the calyx is generally smaller than the corolla with segments of an upwards attitude, however the average size of the calyx itself is smaller in 'Eves Joy' than 'Eves Delight 2'. The size of its flowers for 'Eves Joy' are also smaller in size than 'Eves Delight 2' and have a tighter arrangement of petals.

Another noticeable difference between the two varieties is that 'Eves Joy' has stipules which are generally both longer and much more heavily pigmented with anthocyanin coloration than 'Eves Delight 2'. In the stolons, the anthocyanin concentration is medium in strength for both varieties, but the pubescence on them is weaker in 'Eves Joy'.

BRIEF DESCRIPTION OF THE DRAWINGS

The accompanying color photographs illustrate the overall appearance and distinct characteristics of the new *Fragaria*. The photographs were taken of three-month-old plants of 'Eves Joy' as grown on tabletops in coir bags under tunnels with polyethylene covers in Faversham, Kent, United Kingdom.

The photograph in FIG. 1 provides a view of the plant habit of 'Eves Joy' and fruit in various stages of development.

Figure 1:
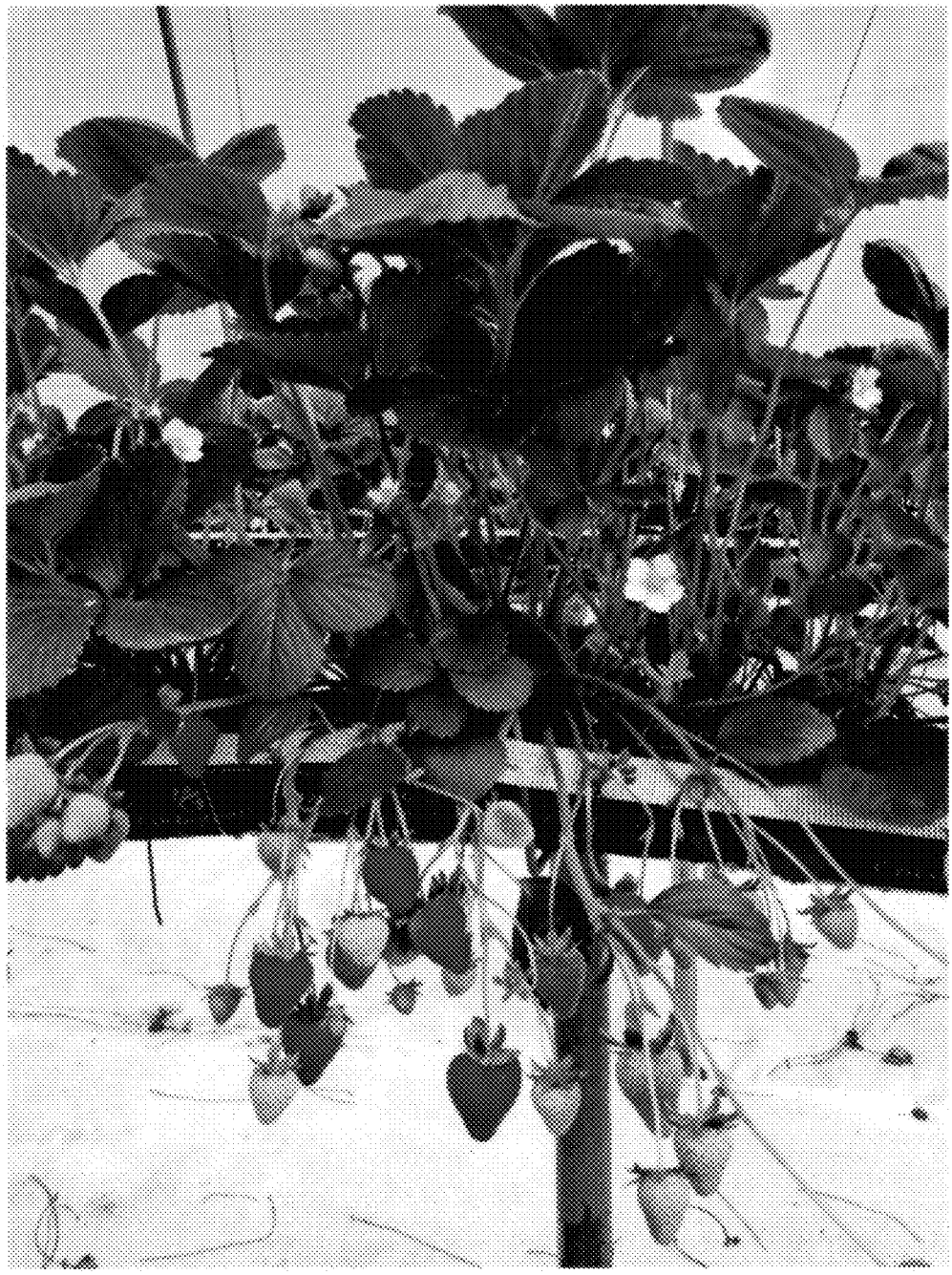
Figure 2:
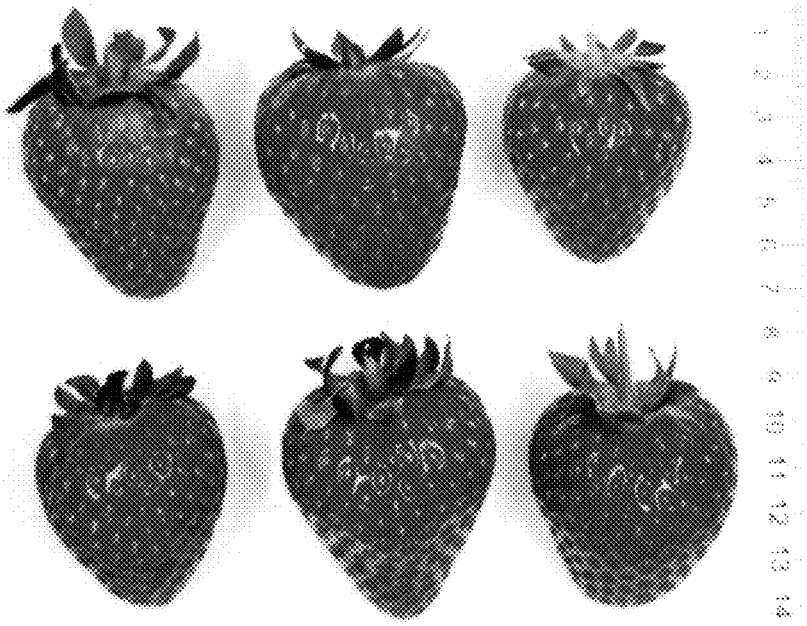

The photograph in FIG. 2 provides a close-up view of the berries of 'Eves Joy'.

Figure 3:
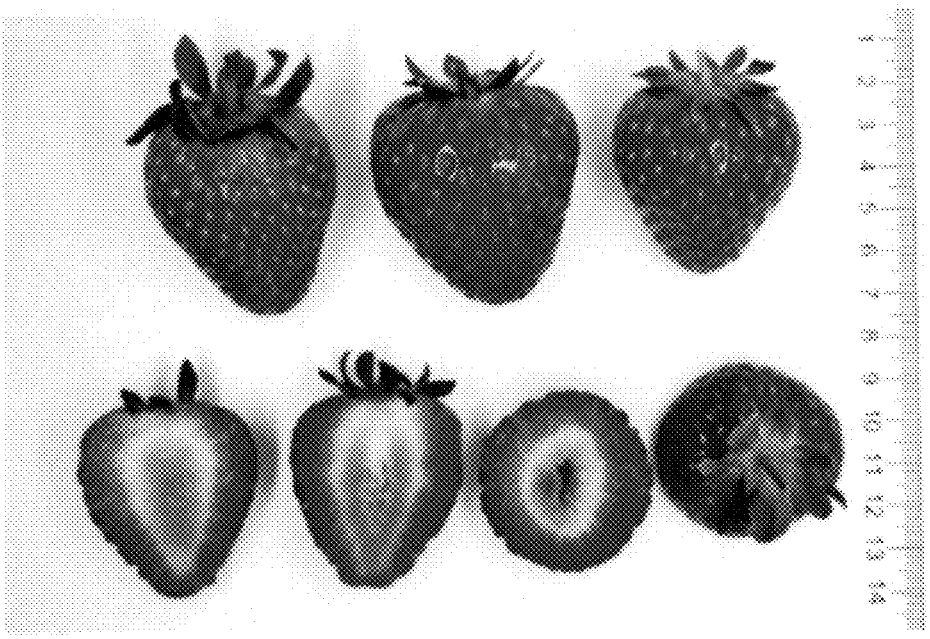

The photograph in FIG. 3 provides a close-up view of the berry flesh of 'Eves Joy'.

Figure 4:
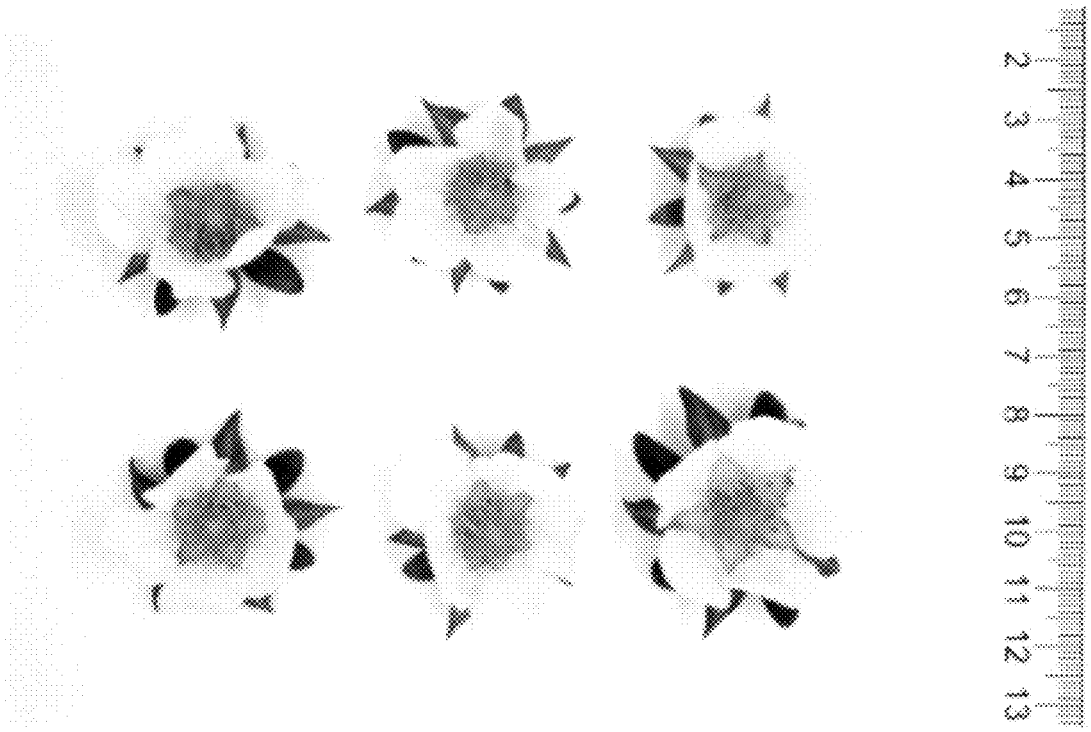

The photograph in FIG. 4 provides a close-up view of the flowers of 'Eves Joy'.

The photographs depict color features as true as is reasonably possible with the digital photography methods used and the color values cited in the detailed botanical description accurately describe the new *Fragaria*.

DETAILED BOTANICAL DESCRIPTION

The following is a detailed description of three-month-old plants of 'Eves Joy' as grown on tabletops in coir bags under tunnels with polyethylene covers in Faversham, Kent, United Kingdom. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—Starting April and produced throughout summer in Faversham, Kent, United Kingdom.

*Plant type.*—Herbaceous fruit producing perennial.

*Plant habit.*—Semi-upright, with medium to sparsely dense canopy.

*Height and spread.*—Medium in size; reaches an average of 42 cm in height and 7.3 cm in width.

*Cold hardiness.*—Not tested in areas where temperatures of less than 32° F. occur.

*Diseases.*—Tolerance to *Botryotinia cinerea* and slight susceptibility to *Podosphaera leucotricha* (powdery mildew) has been observed.

*Root description.*—Fibrous, NN155D in color.

*Root development.*—2 weeks to initiate roots, 5 weeks to produce a young rooted plant.

*Propagation.*—Rooting of stolons and tissue culture.

*Growth rate.*—Vigorous.

*Stem description.*—Acaulescent.

*Stolon description.*—Produces very few stolons throughout the cropping season, surface pubescence is sparse and anthocyanin coloration is medium.

Foliage description:

*Leaf division.*—Three leaflets.

*Leaf arrangement.*—Basal.

*Leaf attachment.*—Petiolate.

*Leaflet shape.*—Rounded.

*Mid-tier leaflet size.*—Average of 9.7 cm in length and 9.3 cm in width.

*Leaflet margins.*—Serrate to crenate with an average of 21.6 serrations per leaf.

*Leaflet base.*—Acute.

*Leaflet apex.*—Round.

*Leaflet glossiness.*—Both surfaces glossy.

*Leaflet aspect.*—Concave.

*Leaflet interveinal blistering.*—Low.

*Leaflet venation.*—Pinnate, coloration matched leaflet color.

*Leaflet surface.*—Upper surface glabrous, lower surface very slightly pubescent, particularly along the vein.

*Leaflet color.*—Upper surface 137A, lower surface 148B, no variegation present on either surface.

*Petiole.*—Round in shape, average of 25.3 cm in length and 4.3 mm in width, 114B in color, surfaces are moderately pubescent.

*Petiolules.*—Round in shape, average of 2.9 cm in length and 2.7 mm in width, moderately pubescent surface, 145A in color.

*Stipule.*—Average of 3.2 cm in length and 2.2 cm in width, 52C in color.

Flower description:

*Inflorescence.*—Truss.

*Inflorescence size.*—Medium to long in length; average of 30.5 cm in length (average of 25 cm before branching) and 0.5 cm in width.

*Flower initiation and expression conditions.*—Temperature dependent.

*Time of flowering* (50% *of plants at first flower*).—Early season.

*Number of flowers per truss.*—Average of 6.

*Flower position relative to foliage.*—Mostly beneath the level of the leaf canopy.

*Flower size.*—Average of 3.27 cm in diameter and 1.9 cm in depth.

*Flower fragrance.*—Slight, weak.

*Calyx.*—Average of 2.4 cm in diameter, smaller than corolla.

*Sepals.*—Average of 10, oblanceolate in shape, obtuse base, acute apex, an average of 2.3 cm in length and 1 cm in width, color; 143B, abaxial color early in the season 145A, later in the season 141C, truncate base, acuminate to acute apex, both surfaces pubescent, position; mixed arrangement relative to the fruit, most re-curving, some horizontal with fruit shoulder.

*Petals.*—Average of 5, average of 1.1 cm in length and 1.14 cm in width, round in shape, acute base, obtuse apex, touching in arrangement, entire margins, upper and lower surface glabrous and NN155A in color.

*Peduncle.*—N144C in color, densely pubescent surface; hair attitude is upwards, strong in strength, average of 25 cm in length and 5 mm in width.

*Pedicel.*—Color; earlier in the season 145A, later in the season N144D, moderately pubescent surface; hair attitude is upwards, strong in strength, average of 5.5 cm in length and 2.1 mm in diameter.

*Gynoecium.*—Average of 4.5 mm in height and 5.4 mm in width, with a steeply dome shaped and slightly pointed top, multiple simple pistils present with capitate shaped stigma, stigma color 1A.

*Androecium.*—Stamens; average of 13, anthers; oval in shape, 1 mm in length, 14A in color in early season and changing to 13B, filament; 1 mm in length and 154A in color, pollen; moderate in quantity, 2A in color.

*Bracts.*—Observed on majority of the flower trusses from early developmental stage, which progresses into a small single leaflet as the truss matures and fruit develops with characteristics similar to leaflets.

Fruit description:

*Shape.*—Predominantly conical, shape is similar for primary, secondary and tertiary fruit.

*Season of harvest.*—May through to End September in Faversham, Kent.

*Time of ripening* (50% *of plants with first ripe fruit*).—Early.

*Type of bearing.*—Everbearing.

*Size.*—Large; an average of 4.44 cm in length and 3.91 cm in width.

*Surface.*—Smooth, medium to highly glossy.

*Calyx position.*—Mostly level with fruit and mostly re-curved.

*Attitude of calyx segments.*—Mostly re-curved with strong adherence to the fruit.

*Diameter of calyx relative to fruit diameter.*—Calyx is the same to slightly smaller in size than the fruit diameter.

*Glossiness.*—Medium to strongly glossy.

*External color* (*skin*).—N45A, color is retained throughout the cropping season.

*Internal color* (*flesh*).—Near skin; 42A, near center; 42B.

*Evenness of color of skin.*—Very even.

*Evenness of color of flesh.*—Paler near center.

*Acidity.*—Low. Total titratable acid average of 0.5% over three seasons in trials.

*Sweetness.*—High.

*Soluble solids.*—Average of 9° over three seasons in trials.

*Firmness.*—Skin is firm (resistant to bruising), flesh is firm.

*Juiciness.*—High.

*Aroma.*—Slight.

*Weight.*—Average of 20.9 g per berry and 1,642 g per plant from late May to end of September over three seasons in trials.

*Hollow center.*—Slight on primary, secondary and tertiary fruit, generally more prominent on primary fruit.

*Shelf life.*—Very good, at least 7 days in cold storage.

*Achene color.*—34A and changing to 3A when mature.

*Achene position.*—Majority below the surface.

*Achene number.*—An average of 251 per berry.

*Band within achenes.*—Absent.

*Fruit use.*—Primarily fresh fruit market.

It is claimed:

1. A new and distinct cultivar of *Fragaria* plant named 'Eves Joy' as herein illustrated and described.

* * * * *